United States Patent [19]
Tagami et al.

[11] Patent Number: 5,508,427
[45] Date of Patent: Apr. 16, 1996

[54] BISIMIDE COMPOUND AND PROCESS FOR THE PRODUCTION THEREOF

[75] Inventors: Toshio Tagami; Yukinori Sakumoto; Takeshi Hashimoto, all of Shizuoka, Japan

[73] Assignee: Tomoegawa Paper Co., Ltd., Tokyo, Japan

[21] Appl. No.: 211,600

[22] PCT Filed: Aug. 6, 1993

[86] PCT No.: PCT/JP93/01126

§ 371 Date: Apr. 6, 1994

§ 102(e) Date: Apr. 6, 1994

[87] PCT Pub. No.: WO94/03460

PCT Pub. Date: Feb. 17, 1994

[30] Foreign Application Priority Data

Aug. 10, 1992 [JP] Japan ..................... 4-232597

[51] Int. Cl.⁶ ..................... C07F 7/10; C08F 10/00; C07D 207/448
[52] U.S. Cl. ..................... 548/406; 556/419; 548/110; 548/549
[58] Field of Search ..................... 548/110, 406; 556/419

[56] References Cited

U.S. PATENT DOCUMENTS

| | | | |
|---|---|---|---|
| 3,558,741 | 1/1971 | Holub et al. | 548/406 |
| 4,565,873 | 1/1986 | Lohmann et al. | 548/110 |
| 4,581,461 | 4/1986 | Rossi et al. | 548/406 |
| 4,806,608 | 2/1989 | Klemarczyk | 526/262 |
| 4,847,343 | 7/1989 | Barthblemy et al. | 526/262 |
| 5,106,988 | 4/1992 | Greco | 548/110 |

Primary Examiner—Floyd D. Higel
Attorney, Agent, or Firm—Wenderoth, Lind & Ponack

[57] ABSTRACT

A bisimide compound of the following general formula (I).

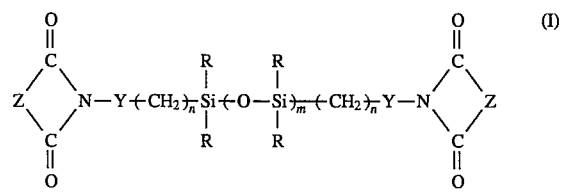

(wherein each of the R's is an alkyl group having 1 to 4 carbon atoms, a phenyl group or a phenyl group substituted with an alkyl or alkoxy group having 1 to 4 carbon atoms, a plurality of these R's may be the same or different, each of the Z's is

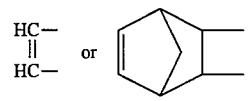

a plurality of these Z's may be the same or different, Y is an arylene group or an aryleneoxy group whose terminal oxygen atom bonds to $(CH_2)_n$, n is an integer of 0 to 20, and m is an integer of 1 to 30.), and a process for the production of the above bisimide compound, which comprises reacting a bisamic acid corresponding to this bisimide compound in a cyclodehydration reaction.

3 Claims, 3 Drawing Sheets

BISIMIDE COMPOUND AND PROCESS FOR THE PRODUCTION THEREOF

TECHNICAL FIELD

This invention relates to a novel bisimide compound which does not impair heat resistance and which has solubility in general solvents and a low melting point, and a process for the production thereof. More specifically, it relates to a bisimide compound having a main skeleton containing a siloxane structure and a process for the production thereof.

TECHNICAL BACKGROUND

A bisimide compound is a raw material which has been and is used in various fields as a precursor for a thermosetting, adduct-type polyimide resin. This compound overcomes the incompleteness of imidation which is a problem in using a linear polyimide resin obtained via a conventional polyamic acid. When the imidation is incomplete, that is, when the inclosure ratio of imide group is low, the glass transition point (Tg) decreases to decrease the heat resistance, and the resistance to hydrolysis decreases. This bisimide compound is also a raw material which has processability almost equivalent to that of an epoxy resin and is widely used in a hot melt, a prepreg and a vulcanizer for rubbers.

A maleimide resin obtained from a bisimide compound typified by N,N'-(methylene-di-p-phenylene)bismaleimide is known as a resin excellent in heat resistance. For example, a polymaleimide resin which is a homopolymer of bismaleimide, or a polymaleimide-polyamine resin which is obtained by polymerization with an amine is widely used in an impregnating varnish, a laminated product and a molding material.

A bisimide compound often has a structure containing an aromatic group which is a rigid structure. There has been therefore a problem in that it is poor in flexibility after being cured and that it is extremely poor in solubility in a solvent. Further, there is also a problem in that it is difficult to adjust the glass transition point thereof. For overcoming the poor solubility in a solvent, attempts have been so far made in various ways, such as an attempt to use a Michel addition reaction between a bisimide compound and an aliphatic diamine or an aromatic diamine or an attempt to design the structure of a diamine as a raw material used for the synthesis of a bisimide.

However, as compared with studies on the solubility, almost no effort has been made to decrease the melting point of a bisimide compound which has not yet cured. If there is provided a bisimide compound having excellent solubility in a solvent and having a low melting point, there is an advantage that the adhesion temperature of the bisimide compound can be decreased, etc.

For decreasing the reel ting point of a bisimide compound, there is a method in which a structure rich with flexibility such as an alkylene structure is introduced into the main skeleton in place of an aromatic ring which is a rigid structure. However, it is very difficult to use aliphatic diamines as raw materials for the bisimide compound, since the aliphatic diamines have high reactivity. That is, it is known that the aliphatic diamines undergo undesirable side reactions to have high molecular weights. For this reason, for the general synthesis of a bisimide compound, an aromatic diamine is generally used as a raw material. That is, a generally synthesized bisimide compound has a main skeleton containing the structure of an aromatic diamine.

For decreasing the melting point of this bisimide compound, it has been necessary to introduce a substituent alkyl group into the aromatic ring, or to introduce a long-chain alkylene group as a binding group between aromatic rings. In these cases, however, the solubility in a solvent has been insufficient.

It is an object of the present invention to provide a novel bisimide compound having a decreased melting point, and a process for the production thereof. It is a further object of the present invention to provide a novel bisimide compound which does not impair high-temperature stability such as temperature for heat decomposition initiation, has excellent solubility in a solvent and has a decreased melting point.

DISCLOSURE OF THE INVENTION

The prevent invention provides a bisimide compound of the following general formula (I).

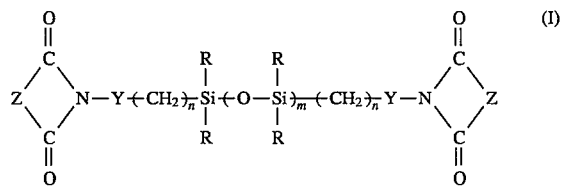

(wherein each of the R's is an alkyl group having 1 to 4 carbon atoms, a phenyl group or a phenyl group substituted with an alkyl or alkoxy group having 1 to 4 carbon atoms, a plurality of these R's may be the same or different, each of the Z's is

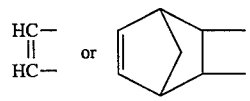

a plurality of these Z's may be the same or different, Y is an arylene group or an aryleneoxy group whose terminal oxygen atom bonds to $(CH_2)_n$, n is an integer of 0 to 20, and m is an integer of 1 to 30.)

Further, the present invention provides a process for the production of a bisimide compound of the above general formula (I), which comprises reacting a bisamic acid of the following general formula (II),

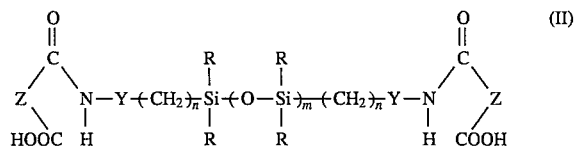

(wherein each of the R's is an alkyl group having 1 to 4 carbon atoms, a phenyl group or a phenyl group substituted with an alkyl or alkoxy group having 1 to 4 carbon atoms, a plurality of these R's may be the same or different, each of the Z's is

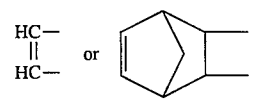

a plurality of the these Z's may be the same or different, Y is an arylene group or an aryleneoxy group whose terminal oxygen atom bonds to $(CH_2)_n$, n is an integer of 0 to 20, and m is an integer of 1 to 30.) in a cyclodehydration reaction, preferably, in the presence of a dehydrating agent and a catalyst.

PREFERRED EMBODIMENTS OF THE INVENTION

Figure 1:
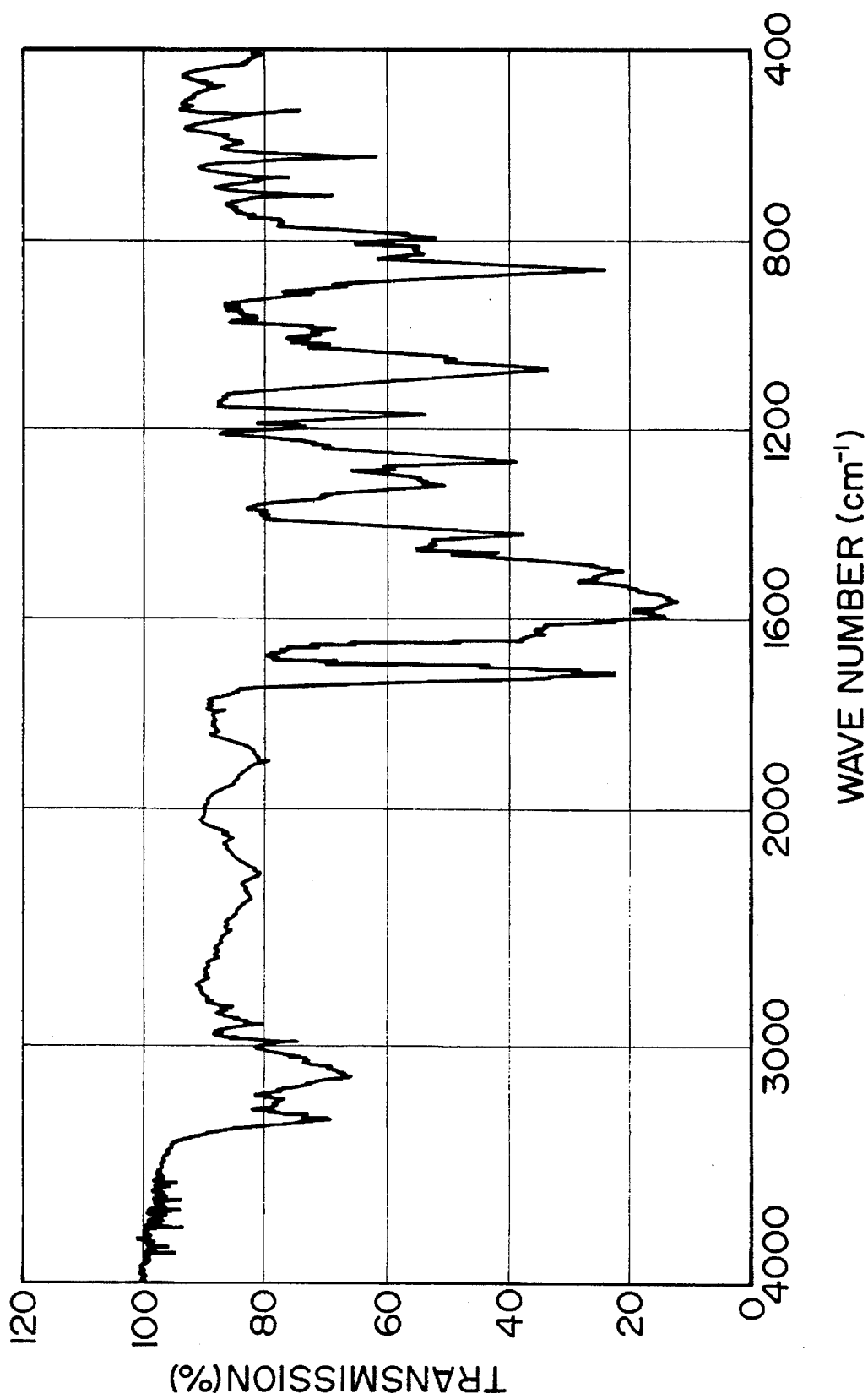
FIG. 1 shows the infrared absorption spectrum of a bismaleamic acid in Example 1.

The present inventors have made diligent studies to overcome the above problems, and as a result, found that a bismaleimide compound having a melting point decreased without impairing high-temperature stability and having excellent solubility in a solvent can be obtained by using halo aromatic diamines having a main skeleton containing a siloxane structure as a starting material for the synthesis of the bisimide compound.

The present invention will be detailed hereinafter.

The bisimide compound of the present invention has the structure of the above general formula (I), and can be produced through the synthesis process of the following reaction formulae. That is, it can be produced by the cyclodehydration of the bisamic acid of the general formula (II) obtained by the synthesis of 2 mole equivalents of an acid anhydride of the following formula (III) and 1 mole equivalent of a siloxane compound having an aromatic amino group in each terminal, represented by the following formula (IV).

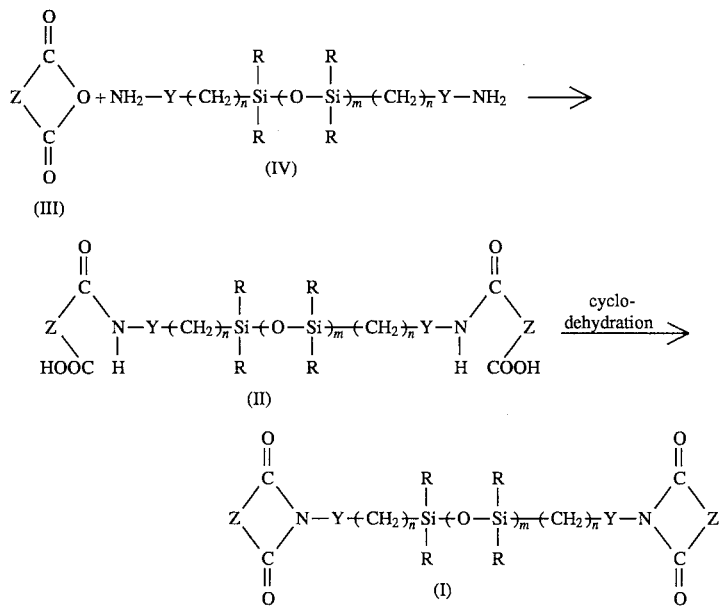

(wherein R, Z, Y, n and m have the same meanings as above.)

The siloxane compound having an aromatic amino group in each terminal, represented by the above formula (IV) and used as one of the raw materials in the present invention, may be produced by any method. Generally, various polysiloxanes having polysiloxane portions having various polymerization degrees can be easily obtained from a polysiloxane of the following formula (V) and an aromatic siliconediamine through the following synthesis scheme. The aromatic siliconediamine can be synthesized by the method described in U.S. Pat. No. 4,882,396.

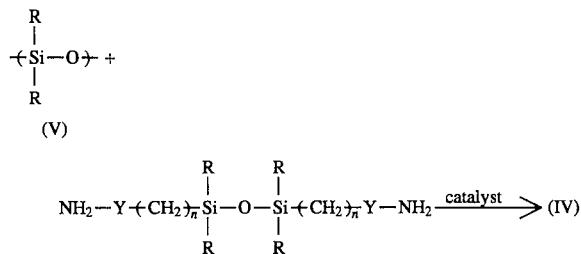

(wherein R, Y and n have the same meanings as above.)

The catalyst used in the above reaction includes platinum-containing catalysts such as platinum black (Pt/C) and chloroplatinic acid, silver-containing catalysts such as halogenated silver, and haloorganic acids typified by trifluoroacetic acid. The polymerization degree of the above siloxane portion (value of m) is 1 to 30, preferably 1 to 20.

The acid anhydride of the above general formula (III) used as one of the raw materials in the present invention is preferably selected from maleic anhydride and nadic anhydride. When the bisimide compound of the present invention is not required to have reactivity, a saturated acid anhydride may be used, and the above acid anhydride is not especially limited.

The organic solvent used for the synthesis of the bisimide compound of the present invention is preferably selected from those which do not take part in the reaction between the acid anhydride and the siloxane compound having aromatic amino group in each terminal.

Specific examples of the organic solvent include halogenated hydrocarbons such as chloroform, methylene chloride, carbon tetrachloride and chlorobenzene, alcohols such as ethylene glycol and benzyl alcohol, hydrocarbons such as cyclohexane, benzene, toluene, xylene, ethylbenzene and butylbenzene, phenols such as phenol, cresol and xylenol, ketones such as acetone, methyl ethyl ketone, cyclohexanone and acetophenone, ethers such as dioxane, tetrahydrofuran, anisole, ethylene glycol dimethyl ether, ethylene glycol monomethyl ether, ethylene glycol monoethyl ether and ethylene glycol monobutyl ether, esters such as butyl acetate, amide-containing solvents such as N,N-dimethylformamide, N,N-dimethylacetamide and N-methyl-2-pyrrolidone, and others such as dimethylsulfoxide. These organic solvents may be used alone or in combination. The organic solvent is preferably used in such an amount that the stirring can be carried out uniformly. The amount of the organic solvent can be 1.1 to 80 times as large as the total amount of the siloxane compound having an aromatic amino group in each terminal and the acid anhydride, and the organic solvent is particularly preferably used in such an amount that the solid concentration is in the range of from 10 to 30% by weight.

In the production of the bisimide compound of the present invention, the reaction conditions for the cyclodehydration are not especially limited, while it is preferred to use a dehydrating agent and a catalyst. The catalyst includes bicarbonate, carbonate, sulfate, nitrate, phosphate, pyrophosphate, acetate and butyrate of sodium or lithium, carbonate, sulfate, chloride, bromide, iodide, formate, acetate, stearate and naphthenate of iron (II and III), nickel (II), manganese (II and III), copper (II and III) or cobalt (II or III) and hydrates of these, and acetylacetonate complex of nickel (II and III), manganese (II and III), copper (II and III) or cobalt (II or III). These catalysts give a sufficient effect when used alone, while at least two of them may be used in combination. Particularly preferred are sodium acetate, nickel acetate and hydrate thereof, and cobalt acetate and hydrate thereof. The amount of the catalyst is not especially limited, and it is sufficient to use it in a catalytic amount.

The dehydrating agent is preferably a compound which reacts with bisamic acid to form an imide group and which itself is hydrated or hydrolyzed, or a compound which has high dehydration capability. Examples of such compounds are as follows. An inorganic compound as the dehydrating agent includes phosphorus pentaoxide, phosphoric acid, polyphosphoric acid, sulfuric anhydride, sulfuric acid, sodium sulfate, calcium oxide and barium oxide. An organic acid as the dehydrating agent includes carboxylic anhydrides such as acetic anhydride, butyric anhydride, propanoic anhydride, succinic anhydride, valeric anhydride, glutaric anhydride and benzoic anhydride and p-toluenesulfonic acids.

In the present invention, tertiary amines may be used as a reaction accelerator. The reaction accelerator includes trialkylamines having an alkyl group having 3 to 20 carbon atoms such as trimethylamine, triethylamine and tributylamine, N,N-diethylcyclohexylamine, N,N-dimethylbenzylamine, N-methylpiperidine, 1,8-diazabicyclo[5,4,0]-7-undecene, 1,4-diazabicyclo[2,2,2]-octane and N-methylmorpholine. These amines may be used alone or in combination. When the reaction accelerator is used, the amount thereof based on the bisamic acid is preferably in the range of from 0.05 to 0.6 mol equivalent, while it may be used in an excess amount.

The cyclodehydration reaction can be carried out by heating in the absence of a catalyst. In this case, however, an increase in molecular weight is liable to take place together with the cyclodehydration reaction. It is hence preferred to use the catalyst.

The temperature for the cyclodehydration reaction in the present invention differs depending upon the catalyst used, while it is generally in the range of from room temperature to the reflux temperature of the organic solvent. The reaction time is required to be at least 1 hour long, and in most cases, the reaction comes to an end within 48 hours.

After the reaction, the reaction mixture is cooled and the resultant homogeneous solution is treated to obtain the bisimide compound of the present invention. The bisimide compound, depending upon the length of siloxane chain, is obtained as a compound having the properties and form of a viscous liquid or a powder.

When the bisimide compound is obtained as a powder, the reaction mixture is dropwise added to water to precipitate it, and the end product is obtained as a precipitate. Then, for removing the catalyst, dehydrating agent, etc., the precipitate may be purified as required.

When the bisimide compound is obtained as a viscous liquid, the reaction mixture is poured into water to form a tar-like product, and the tar-like product is separated from water. Then, the tar-like product is dissolved in an organic solvent which is highly volatile and sparingly soluble in water, and then fully washed with water. Thereafter, the organic solvent is distilled off, and the product is vacuum-dried to obtain the end product.

The bisimide compound of the present invention is suitable for use in an adhesive for electronic materials such as an adhesive layer of a tape for fixing a lead frame, an adhesive of a tape for TAB and an adhesive resin for die bonding.

EXAMPLES

The present invention will be explained hereinafter with reference to Examples. However, the present invention shall not be limited only to these Examples.

Example 1

1) Synthesis of bismaleamic acid

A one-liter, four-necked, flat-bottom flask having a reflux cooling tube with balls therein and a mechanical stirrer was charged with 43.14 g (0.44 mol) of maleic anhydride and 130 g of acetone, and the maleic anhydride was dissolved in the acetone by stirring at room temperature. Then, a solution of 75.3 g (0.20 mol) of bis (3-aminophenoxyphenyl)tetramethyldisiloxane in 100 g of acetone was added dropwise through a dropping funnel over 2 hours while maintaining the internal temperature of the reactor at 25° to 35° C., and the reaction was further continued for 6 hours in the same state. After the reaction, the precipitate was recovered by filtration, and the resultant solid was washed with 1 liter of acetone three times to remove an excess amount of maleic anhydride and vacuum-dried to give purified bismaleamic acid in a nearly quantitative amount.

FIG. 1 shows the result of the infrared absorption spectrum thereof. As shown in FIG. 1, the following absorptions were observed. 3,292–3,215 $cm^{-1}$ (amide N—H extension and shrinkage), broad absorption starting from the vicinity of 2,200 $cm^{-1}$ (absorption inherent to carboxyl group), 3,104 $cm^{-1}$ (absorption based on aromatic C—H extension and shrinkage), $3,034^{-1}$ (C—H extension and shrinkage based on double bond of maleic acid portion), 848, 2,822–2,962 $cm^{-1}$ (absorption based on C—H extension and shrinkage of methyl group on silicon), 1,708 $cm^{-1}$ (absorption derived from carboxyl group of amide portion), and 1,056 $cm^{-1}$ (absorption based on siloxane skeleton).

2) Synthesis of bismaleimide 37.2 Grams (0.065 mol) of the above bismaleamic acid was placed in a 1-liter, four-necked flask, and 92 g of acetone was added to prepare a slurry. Then, 3.0 g of triethylamine was added, and the mixture was stirred for some time. 0.13 Grams of manganese oxide and 0.013 g of cobalt acetate tetrahydrate were consecutively added, and 16 g of acetic anhydride was added at 25°±10° C. over 1 hour. In this state, the mixture was stirred overnight to give a homogeneous reaction solution. The reaction solution was poured into a large amount of water to give the intended product. The intended product was recovered by filtration, washed and dried under reduced pressure to give purified bismaleimide at a yield of 98.7%.

Figure 2:
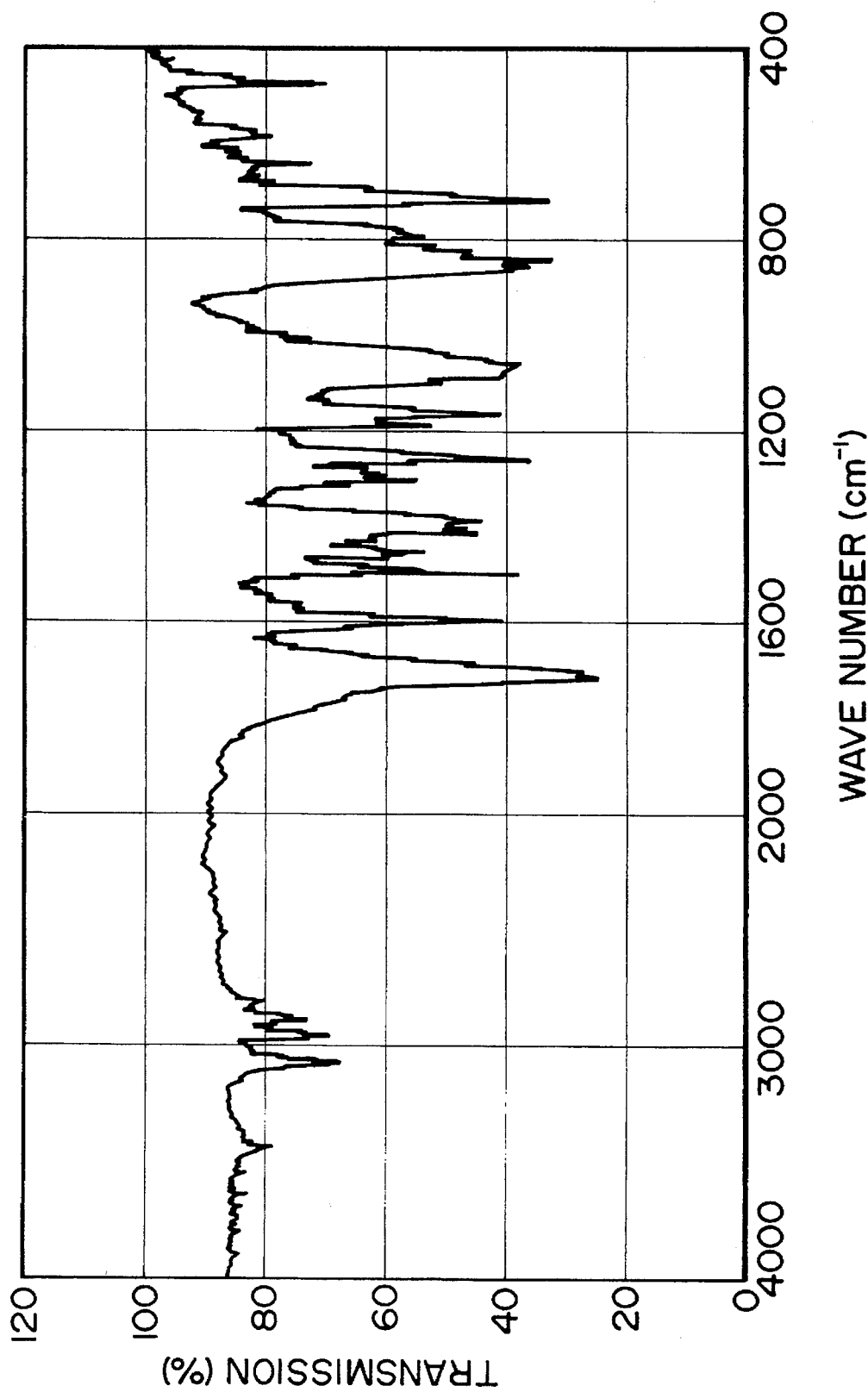
FIG. 2 shows the infrared absorption spectrum of bismaleimide in Example 1.

FIG. 2 shows the result of the infrared absorption spectrum thereof. As shown in FIG. 2, the following absorptions were observed. 3,461 cm$^{-1}$ (overtone of imidecarbonyl group), around 3,096 cm$^{-1}$ (absorption of C—H extension and shrinkage based on double bond of maleic acid portion, and absorption based on aromatic C—H extension and shrinkage), 845, 2,821–2,963 cm$^{-1}$ (absorption based on C—H extension and shrinkage of methyl group on silicon), 1,712 cm$^{-1}$ (absorption derived from imidecarbonyl group), and 1,066 cm$^{-1}$ (absorption based on siloxane skeleton). No absorption based on the amidecarboxylic acid (clearly, broad absorption starting from the vicinity of 2,200 cm$^{-1}$ and absorption at 1,500–1,590 cm$^{-1}$ disappeared) was observed, and it was found that the dehydration/ring-closing reaction had completely proceeded.

The above product had a melting point of 94° C. and a thermal decomposition initiation temperature of 430° C. In addition, the melting point and the thermal decomposition initiation temperature were measured with a thermogravimetric analyzer (TG/DTA 320 type) supplied by Seiko Instruments, Inc. Incidentally, a bismaleimide having a main skeleton containing an aromatic ring (trade name "MB-3000H", supplied by MITSUBISHI PETROCHEMICAL COMPANY, LTD.) had a melting point of 151.3° to 158.8° C. and a heat decomposition initiation temperature of 500° C.

The bismaleimide obtained in the above Example was soluble in methanol, 2-propanol, acetone, methyl ethyl ketone, benzene, toluene, dimethylformamide and N-methylpyrrolidone. In contrast, MB-3000H was soluble in only dimethylformamide and N-methylpyrrolidone among the above solvents.

The following is an example in which the above-obtained bismaleimide was used in an adhesive tape for fixing lead pins of a lead frame.

a. Preparation of coating composition

| | |
|---|---|
| Bismaleimide obtained in Example 1 | 100 parts by weight |
| Nitrilebutadiene rubber (trade name "NIPOL 1001", supplied by Nippon Zeon Co., Ltd.) | 100 parts by weight |
| Peroxide (trade name "Perbutyl P", supplied by NOF Corporation) | 5 parts by weight |
| Methyl ethyl ketone | 400 parts by weight |

A blend of the above components was fully stirred to prepare a coating composition.

b. Preparation of coating surface

The coating composition was applied to a 50 μm thick polyimide film (trade name "Kapton 200H", supplied by Toray-Du Pont K.K.) with a bar coater. Then, the solvent was removed in a hot air-circulating oven under the conditions of 150° C./5 minutes to prepare a coating surface in B-stage.

c. Adhesion to lead frame

A lead frame was placed on a hot plate having a temperature of 180° C., the tape was placed on the lead frame, and the tape was bonded to the lead frame under heat and pressure with a manual roller having a weight of 2 kg.

d. Assembly of package

A resting chip was bonded onto a die pad of the lead frame, followed by wire bonding. Then, the chip was sealed by a resin molding method to give a semiconductor device.

e. Evaluation of reliability

The semiconductor device was allowed to stand under the conditions of 100%R-H, 121° C. and 2 atm. pressure for 1,000 hours. Then, the semiconductor device was measured for a current leak value between pins to show 1×10$^{-1}$ ampere or less, and there was no problem.

Example 2

Bismaleamic acid was obtained in the same manner as in Example 1 except that acetone was replaced with toluene, and the dehydration/ring-closing reaction was carried out in the presence of p-toluenesulfonic acid at 126° C. The resultant product was washed and dried by conventional methods to give bismaleimide at a yield of 98.6%. The bismaleimide was analyzed to show the same results as those in Example 1.

Example 3

Figure 3:
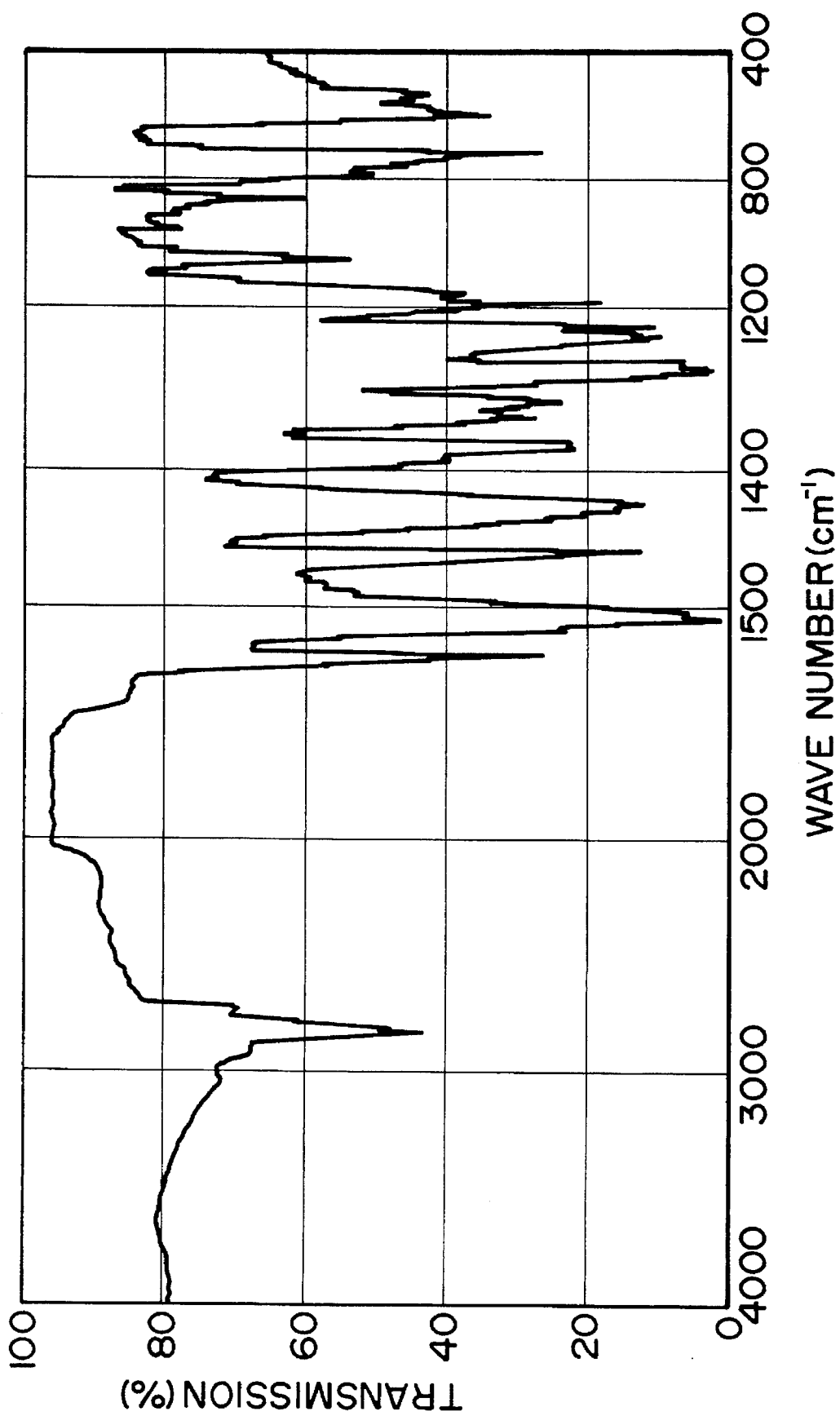
FIG. 3 shows the infrared absorption spectrum of bisnadicimide in Example 3.

The same reaction as that in Example 1 was carried out except that the maleic anhydride in Example 1 was replaced with 5-norbornene-2,3-dicarboxylic anhydride (Nadic acid anhyide) to give bisnadicimide at a yield of 95.3%. FIG. 3 shows the results of infrared absorptions thereof.

Example 4

The same reaction as that in Example 2 was carried out except that the maleic anhydride in Example 1 was replaced with 5-norbornene-2,3-dicarboxylic anhydride (Nadic acid anhydride) to give bisnadicimide at a yield of 96.8%. The bisnadicimide was analyzed to show the same results as those in Example 3.

UTILIZABILITY IN INDUSTRY

The bisimide compound of the present invention has excellent solubility in an organic solvent and has a decreased melting point as compared with conventional thermosetting imide compounds. This compound is very useful as a polyimide-containing resin precursor. Further, according to the present invention, the flexibility of the cured product can be controlled by adjusting the polymerization degree of the siloxane portion, and the bisimide compound of the present invention can be applied in broad fields. For example, it can be used in an adhesive tape for electronic materials or integrated into a semiconductor device.

We claim:

1. A bisimide compound having the following formula (I):

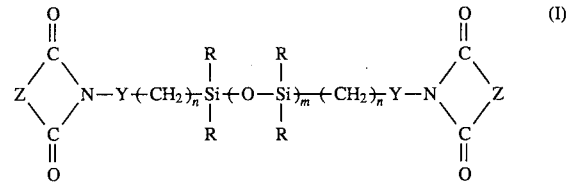

wherein each R is independently alkyl having 1 to 4 carbon atoms, phenyl or phenyl substituted with alkyl or alkoxy having 1 to 4 carbon atoms, n is an integer from 0 to 20, m is an integer from 1 to 30, Y is

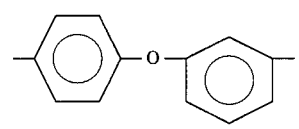

and Z is

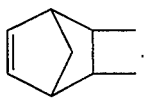

2. A process for the production of a bisimide compound having the following formula (I):

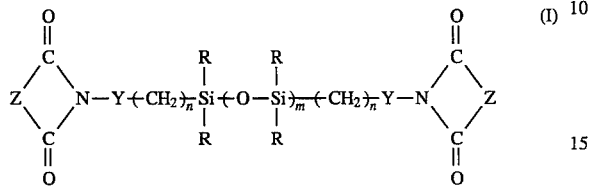

which comprises cyclizing a bisamic acid having the following formula (II) in the presence of a catalyst and a dehydrating agent at a temperature in the range from room temperature to a reflux temperature of an organic solvent:

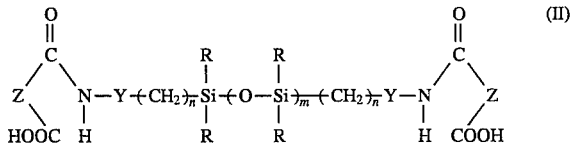

wherein in formulas (I) and (II), each R is independently alkyl having 1 to 4 carbon atoms, phenyl or phenyl substituted with alkyl or alkoxy having 1 to 4 carbon atoms, n is an integer from 0 to 20, m is an integer from 1 to 30, Y is

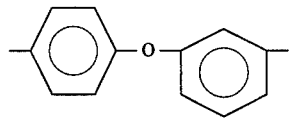

or aryleneoxy, and each Z is independently

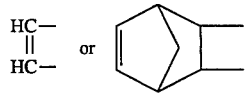

provided that when Y is aryleneoxy the terminal oxygen atom of the aryleneoxy bonds to $(CH_2)_n$, the dehydrating agent being at least one agent selected from the group consisting of phosphorus pentoxide, phosphoric acid, polyphosphoric acid, sulfuric acid, sulfuric anhydride, sodium sulfate, calcium oxide, barium oxide, acetic anhydride, butyric anhydride, propanoic anhydride, succinic anhydride, valeric anhydride, glutaric anhydride, benzoic anhydride, and p-toluenesulfonic acid and the catalyst being at least one catalyst selected from the group consisting of sodium acetate, nickel acetate, cobalt acetate, and hydrates thereof.

3. A process according to claim 2, wherein the dehydrating agent is at least one of acetic anhydride and p-toluenesulfonic acid.

* * * * *